United States Patent
Ardenkjaer-Larsen et al.

(10) Patent No.: US 6,311,086 B1
(45) Date of Patent: Oct. 30, 2001

(54) OVERHAUSER MAGNETIC RESONANCE IMAGING (ORMI) METHOD COMPRISING EX VIVO POLARIZATION OF A MAGNETIC RESONANCE (MR) IMAGING AGENT

(75) Inventors: Jan Henrik Ardenkjaer-Larsen; Klaes Golman; Georg Hansson; Ib Leunbach; Stefan Petersson; Lars-Goran Wistrand; Oskar Axelsson, all of Oslo (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 09/460,094

(22) Filed: Dec. 13, 1999

Related U.S. Application Data

(63) Continuation of application No. PCT/GB98/01814, filed on Jun. 19, 1998.
(60) Provisional application No. 60/076,924, filed on Mar. 5, 1998.

(30) Foreign Application Priority Data

Jun. 19, 1997 (GB) .................................................. 9712984
Jan. 5, 1998 (GB) .................................................. 9800158

(51) Int. Cl.[7] ...................................................... A61B 5/05
(52) U.S. Cl. ........................... 600/420; 324/307; 324/309
(58) Field of Search ................................... 600/407, 409, 600/410, 412, 414, 420, 436; 514/9, 11, 15; 324/309, 300, 307; 424/9.3

(56) References Cited

U.S. PATENT DOCUMENTS

| | | | |
|---|---|---|---|
| 5,263,482 | 11/1993 | Leunbach | 128/653.2 |
| 5,479,925 | 1/1996 | Dumoulin et al. | 128/653.3 |

FOREIGN PATENT DOCUMENTS

| | | | |
|---|---|---|---|
| WO 98 01766 A | 1/1998 | (WO) . | |

OTHER PUBLICATIONS

"The Use of Dynamically Polarized Contrast Agents" Research Disclosure, 348, Apr. 1993, XP002070308.

Gerfen G.J. et al., "High frequency (140 Ghz) dynamic nuclear polarization; Polarization transfer to a solute in frozen aqueous solution", Journal of Chemical Physics, Jun. 22, 1995, XP002077806.

*Primary Examiner*—Marvin M. Lateef
*Assistant Examiner*—Eleni Mantis Mercader
(74) *Attorney, Agent, or Firm*—Bacon & Thomas

(57) ABSTRACT

This invention provides a method of MR investigation of a sample, the method comprising: (i) placing in a uniform magnetic field a composition comprising an OMRI contrast agent and an MR imaging agent containing nuclei (MR imaging nuclei) capable of emitting magnetic resonance signals (e.g. the primary magnetic field $B_0$) and capable of exhibiting a $T_1$ relaxation time of 6 s or more (at 37° C. in $D_2O$ in a field of 7T); (ii) exposing the composition to a first radiation of a frequency selected to excite electron spin transitions in the OMRI contrast agent; (iii) optionally but preferably separating the whole, substantially the whole, or a portion of said OMRI contrast agent from said MR imaging agent; (iv) administering said MR imaging agent to said sample, (v) exposing the sample to a second radiation of a frequency selected to excite nuclear spin transitions; (vi) detecting magnetic resonance signals from the sample; and (vii) optionally, generating an image or dynamic flow data from the detected signals.

12 Claims, 2 Drawing Sheets

Figure 1:
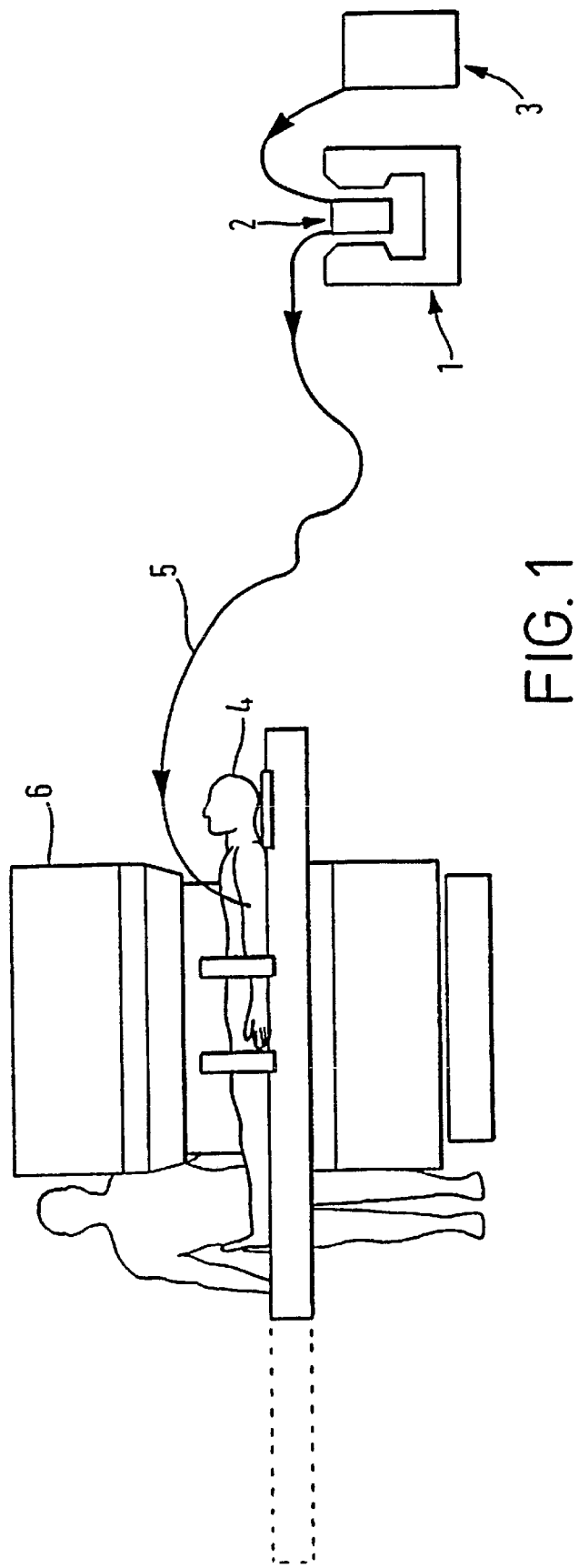

OVERHAUSER MAGNETIC RESONANCE IMAGING (ORMI) METHOD COMPRISING EX VIVO POLARIZATION OF A MAGNETIC RESONANCE (MR) IMAGING AGENT

This application is a continuation of pending international application number PCT/GB98/01814 filed Jun. 19, 1998 (of which the entire disclosure of the pending, prior application is hereby incorporated by reference), which itself is a continuation-in-part of U.S. provisional application Ser. No. 60/076,924 filed Mar. 5, 1998, benefit of which is claimed under 35 USC 119(e).

Magnetic resonance imaging (MRI) is a diagnostic technique that has become particularly attractive to physicians as it is non-invasive and does not involve exposing the patient under study to potentially harmful radiation such as X-rays.

Electron spin resonance enhanced MRI, referred to herein as OMRI (Overhauser MRI) but also referred to in earlier publications as ESREMRI or PEDRI, is a method of MRI in which enhancement of the magnetic resonance signals from which images may be generated is achieved by virtue of dynamic nuclear polarization (the Overhauser effect) that occurs on VHF stimulation of an ESR transition in a magnetic (usually paramagnetic but optionally for example superparamagnetic) material (hereinafter referred to as an OMRI contrast agent) in the subject under study. Magnetic resonance signal enhancement may be by a factor of a hundred or more thus allowing OMRI images to be generated rapidly and/or with relatively low primary magnetic fields.

OMRI techniques have been described by several authors, notably Leunbach, Lurie, Ettinger, Grücker, Ehnholm and Sepponen, for example in EP-A-296833, EP-A-361551, WO-A-90/13047, J. Mag. Reson. 76:366–370(1988), EP-A-302742, SMRM 9:619(1990), SMRM 6:24(1987), SMRM 7:1094(1988), SMRM 8:329 (1989), U.S. Pat. No. 4,719,425, SMRM 8:816(1989), Mag. Reson. Med. 14:140–147(1990), SMRM 9:617(1990), SMRM 9:612(1990), SMRM 9:121(1990), GB-A-2227095, DE-A-4042212 and GB-A-2220269. Res. Discl. 34833:242 (1993) (anon) discloses that contrast agents can be polarized by means of the Overhauser effect before being injected into the human body. U.S. Pat. No. 5,479,925 (Dumoulin) discloses an imaging system for obtaining vessel-selective NMR angiographic images of a subject, whilst U.S. Pat. No. 5,263,482 (Leunbach) discloses a method of and apparatus for thermographic imaging involving the use in ESREMRI of a paramagnetic contrast agent having in its esr spectrum a temperature dependent transition. One area of particular interest is the use of OMRI in determining oxygen concentrations in a sample (eg. an animate body) and this is the subject of co-pending U.S. patent application Ser. No. 08/540,146 of Leunbach.

In the basic in vivo OMRI technique, the imaging sequence involves initially irradiating a subject placed in a uniform magnetic field (the primary magnetic field, $B_0$) with radiation, usually VHF radiation, of a frequency selected to excite a narrow linewidth ESR transition in an OMRI contrast agent which is in, or has been administered to, the subject. Dynamic nuclear polarization results in an increase in the population difference between the excited and ground nuclear spin states of selected nuclei, i.e. those nuclei, generally protons, which are responsible for the magnetic resonance signals (hereinafter the MR imaging nuclei). Since MR signal intensity is proportional to this population difference, the subsequent stages of each imaging sequence, performed essentially as in conventional MRI techniques, result in larger amplitude MR signals being detected. OMRI contrast agents which exhibit an ESR transition able to couple with an NMR transition of the MR imaging nuclei may be naturally present within the subject (eg. oxygen or melanin) or may be administered thereto.

Contrast agents useful in conventional methods of OMRI and suitable for in vivo administration have been reported in a number of publications. In WO-A-88/10419 (Hafslund Nycomed Innovation AB), for example, various OMRI contrast agents were proposed with particular emphasis on the use of stable nitroxide free radicals, of the chloranil semiquinone radical or of Fremy's Salt. In WO-A-90/00904 (Hafslund Nycomed Innovation AB) the use of deuterated free radicals (e.g. deuterated nitroxide free radicals) as OMRI contrast agents was proposed. WO-A-91/12024 (Nycomed Innovation AB) refers generally to the use of carbon free radicals, i.e. radicals where the unpaired electron or electrons are associated primarily with carbon atoms (for example triarylmethyl radicals where the electron charge is delocalised over a number of aromatic nuclei). More specifically, the use in OMRI of triarylmethyl radicals in which at least one aryl moiety is a sulphur-based heterocycle is the subject of WO-A-96/39367 (Nycomed Imaging AS). The use in OMRI of free radicals in which the electron charge is delocalised through a conjugated carbon-based π-system is referred to in WO-A-93/02711 (Hafslund Nycomed Innovation AB). However, OMRI contrast agents are not limited to paramagnetic organic free radicals and particulate ferromagnetic, ferrimagnetic and superparamagnetic contrast agents have been proposed in UK Patent Application No. 9605482.0, filed on Mar. 15, 1996 in the name of Nycomed Imaging AS.

To be successful as an in vivo OMRI contrast agent in conventional methods of OMRI, a chosen material must have inter alia the property of physiological tolerability. This factor alone imposes a severe limitation on the types of OMRI contrast agent which prove to be of real diagnostic utility. Organic free radicals, for example, are frequently unstable in physiological conditions or have very short half-lives leading to toxicity problems. It will often be the case that a radical found to give excellent Overhauser enhancement factors in vitro cannot be used diagnostically due to its physiological incompatibility. There is therefore a need for improved methods of OMRI which are more flexible, i.e. less constrained by physiological factors.

One particular method of OMRI of a sample is disclosed in U.K. Patent Application No. 9614139.5 filed on Jul. 5, 1996 in the name of Nycomed Imaging AS in which it is possible to avoid administering the whole of, or substantially the whole of, an OMRI contrast agent to a sample whilst still achieving the desired Overhauser enhanced contrast effect. The method relies on ex vivo dynamic nuclear polarisation of selected nuclei of an MR imaging agent (e.g. water) by an OMRI contrast agent, the latter conveniently being disposed of prior to administration of the polarised MR imaging agent into the subject.

The present invention is an improvement on the ex vivo OMRI method which involves using as the MR imaging agent a material having a longer $T_1$ relaxation time than is available from water. Thus, typically an injected bolus would take 10–20 s to reach the right portion of the heart and the lungs. Whereas in this situation the magnetisation of water protons would have decreased to 3.6% of its initial value, the magnetisation of an MR imaging agent exhibiting a $T_1$ value of 10 s would have decreased to 37%. Moreover, the lower concentration in terms of protons available from an MR imaging agent compared to water results in a signal many times stronger than that of an aqueous solution.

Thus viewed from one aspect the present invention provides a method of magnetic resonance investigation of a sample, preferably of a human or non-human animal body (eg. a mammalian, reptilian or avian body), said method comprising:

(i) placing in a uniform magnetic field a composition comprising an Overhauser magnetic resonance imaging (OMRI) contrast agent and a magnetic resonance (MR) imaging agent containing in its molecular structure nuclei capable of emitting magnetic resonance signals, eg. the primary magnetic field $B_0$, and having a $T_1$ relaxation time of 6 s or more, when at 37° C. in $D_2O$ in a field of 7T;

(ii) exposing said composition to a first radiation of a frequency selected to excite electron spin transitions in said OMRI contrast agent and thereby cause a nuclear spin polarisation of said nuclei;

(iii) optionally but preferably separating the whole, substantially the whole, or a portion of said OMRI contrast agent from said MR imaging agent;

(iv) administering said MR imaging agent to said sample;

(v) exposing said sample to a second radiation of a frequency selected to excite nuclear spin transitions;

(vi) detecting magnetic resonance signals from said sample; and (vii) optionally, generating an image or dynamic flow data from said detected signals.

Thus this aspect of the invention involves the sequential steps of ex vivo dynamic nuclear polarisation of MR imaging nuclei, administration of polarised MR imaging nuclei, preferably in the absence of a portion of, or more preferably substantially the whole of, the OMRI contrast agent, and conventional in vivo MR signal generation and measurement. The MR signals obtained in this way may be conveniently converted into image data (eg 2D- or 3D-image data) or flow data. The method according to this aspect of the invention has a number of advantages over known in vivo methods of OMRI, some of which are referred to in detail below.

One of the advantages which the present method offers over conventional methods is that physiological tolerability of the OMRI contrast agent is less of a determining factor in the overall diagnostic utility of the method. Similarly, in conventional methods of OMRI, the diagnostic utility of OMRI contrast agents is subject to the constraints imposed by the physical and chemical characteristics of the administrable media in which the contrast agents are formulated, for example the deleterious effect the OMRI contrast agent may have on viscosity, pH, etc. of the formulation. Once again, the method according to this aspect of the invention is less constrained by such factors because the OMRI contrast agent need not be present in an administrable form. Moreover, factors such as biodegradability and biodistribution, on which the suitability of OMRI contrast agents for use in conventional OMRI methods may stand or fall, are of less importance in determining the suitability of the present invention for in vivo use.

In any conventional OMRI experiment carried out in vivo there will be a number of secondary factors acting to relax the excited spin state back to equilibrium and reduce the amplitude of the MR signal obtained. In particular, MR imaging agents will be subject to local magnetic field inhomogeneities resulting, for example, from the presence of paramagnetic species such as iron (eg. in erythrocytes), or dissolved oxygen in the body fluid or of the radical itself responsible for Overhauser enhancement (i.e. radical self-broadening), all of which serve to increase the rate of relaxation. The relaxation rate will also be dependent on the temperature and chemical nature of the body fluid. The present method however alleviates these problems by providing Overhauser stimulation ex vivo. Thus the method allows the chemical environment, pH and temperature to be optimised by the operator and the effects of local magnetic field inhomogeneities such as those described above to be reduced. Overhauser enhancement is also strongly dependent on the density of the sample (ie. its structure) and in in vivo use there is the added problem of non-uniform radiation penetration into the large sample. This problem of course does not arise in the method according to this aspect of the invention.

The strength of the magnetic field experienced by the composition will directly effect the degree of Overhauser signal. Thus a yet further benefit of the present method is that a much higher magnetic field may be applied ex vivo than is generally possible with in vivo techniques. With in vivo techniques, the strength of the magnetic field has to be reduced due to the poor penetration depth of high RF frequencies in human tissue.

Suitable MR imaging agents may contain nuclei such as protons. However other non-zero nuclear spin nuclei may be useful (eg $^{19}F$, $^3Li$, $^1H$ $^{15}N$, $^{29}Si$, $^{13}C$, or $^{31}P$) and $^{19}F$ and $^{13}C$ nuclei are particularly preferred. In this event the MR signals from which the image is generated will be substantially only from the MR imaging agent itself. The polarised MR imaging agent may have a significant enough effect on in vivo water protons for conventional $^1H$ MRI to be carried out on those protons.

Where the MR imaging nuclei is other than a proton (eg $^{13}C$ or $^{19}F$), there will be essentially no interference from background signals (the natural abundance of $^{13}C$ and $^{19}F$ being negligible) and image contrast will be advantageously high. This is especially true where the MR imaging agent itself is enriched above natural abundance. Thus the method according to the invention has the benefit of being able to provide significant spatial weighting to a generated image. In effect, the administration of a polarised MR imaging agent to a selected region of a sample (eg by injection) means that the contrast effect may be localised to that region. The precise effect of course depends on the extent of biodistribution over the period in which the MR imaging agent remains significantly polarised. In general, specific body volumes (i.e. regions of interest such as the vascular system or specific organs such as the brain, kidney, heart or liver) into which the agent is administered may be defined with improved signal to noise (particularly improved contrast to noise) properties of the resulting images in these volumes.

In one embodiment, a "native image" of the sample (e.g. body) (ie. one obtained prior to administration of the MR imaging agent or one obtained for the administered MR imaging agent without prior polarisation as in a conventional MR experiment) may be generated to provide structural (eg. anatomical) information upon which the image obtained in the method according to the invention may be superimposed. A "native image" is generally not available where $^{13}C$ or $^{19}F$ is the imaging nucleus because of the low abundance of $^{13}C$ and $^{19}F$ in the body. In this case, a proton MR image may be taken to provide the anatomical information upon which the $^{13}C$ or $^{19}F$ image may be superimposed.

Whilst the MR imaging agent may in general be solid or liquid, it should of course be physiologically tolerable or be capable of being provided in a physiologically tolerable, administrable form. Preferred MR imaging agents are soluble in (or be dispersed or suspended in) aqueous media (eg. water) and are of course non-toxic where the intended end use is in vivo.

Conveniently, the MR imaging agent once polarised will remain so for a period sufficiently long to allow the imaging procedure to be carried out in a comfortable time span. Generally sufficient polarisation will be retained by the MR imaging agent in its administrable form (eg. in injection solution) if it has a $T_1$ value (at a field strength of 0.01–7T and a temperature in the range 20–40° C.) of 6s or more, preferably 8s or more, more preferably 10 s or more, especially preferably 15 s or more, more especially preferably 30 s or more, yet more especially preferably 70 s or more, even yet more especially preferably 100 s or more (for example at 37° C. in water at 1T and a concentration of at least 1 mM), for example 8–1000 s, especially 15–500 s, more particularly 70–300 s. The MR imaging agent may be advantageously an agent with a long $T_2$ relaxation time.

The long $T_1$ relaxation time of certain $^{13}C$ nuclei is particularly advantageous and certain MR imaging agents containing $^{13}C$ nuclei are therefore preferred for use in the present method. The γ-factor of carbon is about ¼ of the γ-factor for hydrogen resulting in a Larmor frequency of about 10 MHz at 1T. The rf-absorption and reflections in a patient is consequently and advantageously less than in water (proton) imaging. Preferably the polarised MR imaging agent has an effective $^{13}C$ nuclear polarisation corresponding to the one obtained at thermal equilibrium at 300K in a field of 0.1T or more, more preferably 25T or more, particularly preferably 100T or more, especially preferably 5000T or more (for example 50 kT). MR imaging agents containing $^{19}F$ nuclei are also preferred.

When the electron cloud of a given molecule interacts with atoms in surrounding tissue, the shielding of the atom responsible for the the MR signal is changed giving rise to a shift in the MR frequency ("the chemical shift effect"). When the molecule is metabolised, the chemical shift will be changed and MR imaging agents in different chemical surroundings may be visualised separately using pulses sensitive to chemical shift. When the frequency difference between MR imaging molecules in different surroundings is 150 Hz or higher (corresponding to 3.5 ppm or higher at 1T), the two components may be excited separately and visualised in two images. Standard chemical shift selective excitation pulses may then be utilised. When the frequency separation is less, the two components may not be separated by using frequency selective rf-pulses. The phase difference created during the time delay after the excitation pulse and before the detection of the MR signal may then be used to separate the two components. Phase sensitive imaging pulse sequence methods (Dixon, Radiology, 1984, 153: 189–194 and Sepponen, Mag Res. Imaging, 3, 163–167, 1985) may be used to generate images visualising different chemcial surroundings or different metabolites. The long $T_2$ relaxation time which may be a characteristic of a MR imaging agent will under these circumstances make it possible to use long echo times (TE) and still get a high signal to noise ratio. Thus an important advantage of the MR imaging agents used in the present method is that they exhibit a chemical shift dependent on the local composition of the body in which they are localised. Preferred MR imaging agents will exhibit (at 1T) a chemical shift of more than 2 ppm, preferably more than 1oppm depending on whether the MR imaging agent is localised inside or outside the vascular system. MR imaging agents containing polarised $^{13}C$ nuclei (or $^{19}F$ nuclei) exhibit large changes in chemical shift in response to physiological changes (eg. pH, $pO_2$, $pCO_2$, redox potential, temperature or ionic concentrations of for example $Na^+$, $K^+$, $Ca^{2+}$) or metabolic activity and therefore may be used to monitor these parameters.

Solid MR imaging agents (e.g. $^{13}C$ or $^{19}F$ enriched solids) may exhibit very long $T_1$ relaxation times and for this reason are especially preferred for use in the present method. The $T_1$ relaxation time may be several hours in the bulk phase, although this may be reduced by reduction of grain size and/or addition of paramagnetic impurities eg. molecular oxygen. The long relaxation time of solids advantageously allows the procedure to be conveniently carried out with less haste and is particularly advantageous in allowing the polarised solid MR imaging agent to be stored or transported prior to pharmaceutical formulation and administration. In one embodiment, the polarised MR imaging agent may be stored at low temperature eg in frozen form and prior to administration, the MR imaging agent may be rapidly warmed to physiological temperatures using conventional techniques such as infrared or microwave radiation or simply by adding hot, sterile administrable media eg saline. Such frozen polarised compositions form a further aspect of the invention.

For in vivo use, a polarised solid MR imaging agent may be dissolved in administrable media (eg water or saline), administered to a subject and conventional MR imaging performed. Thus solid MR imaging agents are preferably rapidly soluble (eg. water soluble) to assist in formulating administrable media. Preferably the MR imaging agent should dissolve in a physiologically tolerable carrier (eg water or Ringers solution) to a concentration of at least 1 mM at a rate of 1 mM/$3T_1$ or more, particularly preferably 1 mM/$2T_1$ or more, especially preferably 1 mM/$T_1$ or more. Where the solid MR imaging agent is frozen, the administrable medium may be heated, preferably to an extent such that the temperature of the medium after mixing is close to 37° C.

A polarised MR imaging agent may be administered (either alone or with additional components such as additional MR imaging agents) in liquid form. Liquids generally have slower diffusion which makes it possible to use sequences such as echo planar imaging (EPI). The overall technique will be faster and yield better resolution (voxel size<1 mm) than conventional techniques (voxel size approx. 1–5 mm) at current acquisition times. It will give good images at all fields including in low field (eg. 0.01–0.5T) machines.

Given that the method of the invention should be carried out within the time that the MR imaging agent remains significantly polarised, it is desirable for administration of the polarised MR imaging agent to be effected rapidly and for the MR measurement to follow shortly thereafter. The preferred administration route for the polarised MR imaging agent is parenteral eg by bolus injection, by intravenous, intraarterial or peroral injection. The injection time should be equivalent to $5T_1$ or less, preferably $3T_1$ or less, particularly preferably $T_1$ or less, especially $0.1T_1$ or less. The lungs may be imaged by spray, eg by aerosol spray.

The OMRI contrast agent may also be chosen to be water soluble (eg. typically the water soluble free radicals described in WO-A-93/02711), or capable of being dispersed in water or suspended in water to produce the desired composition for use in the method according to this aspect of the invention. The composition may be conveniently stored in this "ready to use" form prior to use. Thus viewed from a further aspect the present invention provides a kit comprising an aqueous solution or heterogeneous phase composition of an Overhauser magnetic resonance imaging (OMRI) contrast agent and a magnetic resonance (MR) imaging agent said MR imaging agent capable of exhibiting a $T_1$ relaxation time of 6 s or more, together with a means for administering said MR imaging agent to a sample. In a preferred embodiment, the kit comprises an OMRI contrast agent, a means for immobilising said OMRI contrast agent, an MR imaging agent capable of exhibiting a $T_1$ relaxation time of 6 s or more and a means for delivering said MR imaging agent, eg. by a plunger or pressure applicator.

As MR imaging agents in accordance with the invention, particular mention may be made of 1,3,5 tricarboxybenzene.

Viewed from a further aspect the present invention provides an imaging composition comprising an Overhauser magnetic resonance imaging (OMRI) contrast agent and a magnetic resonance (MR) imaging agent having a $T_1$ relaxation time of 6 s or more (at 37° C. in $D_2O$ at a field of 7T).

The method according to this aspect of the invention may be conveniently carried out by using a first magnet for providing the polarising magnetic field and a second magnet for providing the primary magnetic field for MR imaging. Having a separate magnet dedicated to providing the dynamic nuclear polarisation allows the operator advantageously to optimise field strength independently of the MR imaging field. The OMRI apparatus suitable for use in such an embodiment may be standardised as it would be similar for all imaging applications, thereby making it cheap to manufacture and simple to use. Thus, an MR apparatus adapted for use in the method described hereinbefore provides a further aspect of the present invention, said apparatus comprising a first magnet providing a magnetic field for dynamic nuclear polarisation of a fluid and a second magnet providing the primary magnetic field for MR imaging of a subject (eg. an animate subject). FIG. 1 of the accompanying drawings is a schematic representation of one embodiment of the apparatus according to the invention. Therein a freestanding polarising magnet (1) optionally together with a filter surrounds an EPR resonator (2) which provides the nuclear polarisation. A container (3) comprising a pump is provided for carrying the contrast composition which is delivered to a subject (4) by a delivery line (5). The subject is situated within a conventional MR scanner (6).

Figure 2:
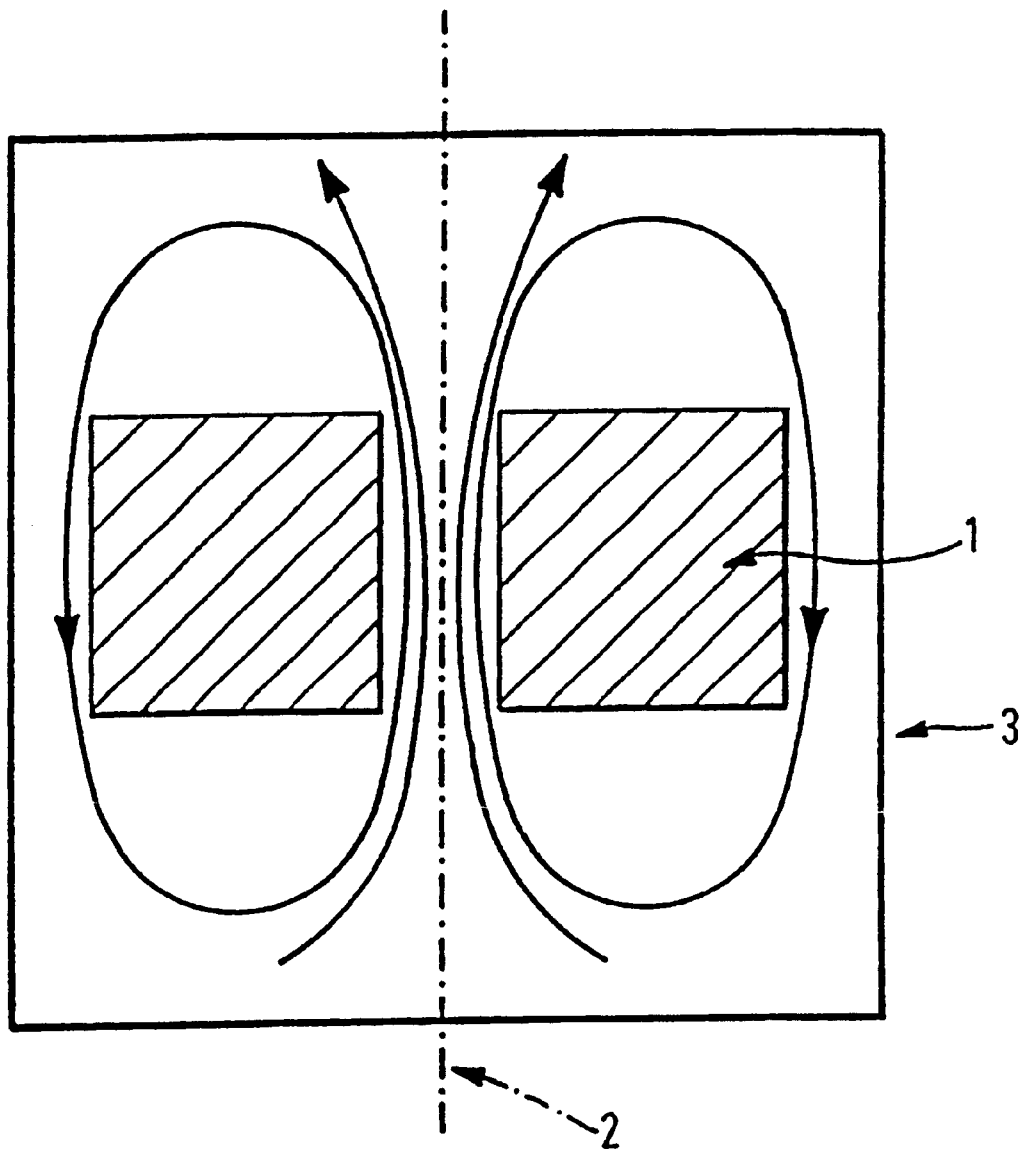

In one embodiment of the method and apparatus according to this aspect of the invention, a dielectric resonator may be used in the dynamic nuclear polarisation process. Generally speaking, dynamic nuclear polarisation requires a volume with a fairly strong high frequency magnetic field and an accompanying electric field which is made as small as possible. A dielectric resonator may be used to provide a preferred field arrangement in which the magnetic field lines are shaped like a straw in a sheaf of corn with an electric field forming circles like the thread binding the sheaf. A field arrangement of this type may be formed by one of several rings or tubes of a material with a high dielectric constant and low loss. The man skilled in the art will appreciate that such a tube will exhibit different electromagnetic resonant modes. One of the dominant modes has the desired characteristic of electric field circulating around the tube axis within the wall and being zero at the axis and everywhere perpendicular to it. The magnetic field on the other hand is concentrated around the tube axis and mainly directed along it. The composition to be polarised is conveniently placed inside the resonator which is itself placed inside a metal box with a clearance typically of the order of the size of the resonator, and is excited to the desired resonance with a coupling loop or the like. The metal box ensures that the electromagnetic energy does not leak away by radiation. FIG. 2 of the accompanying drawings shows a dielectric resonator (1) (with an axis of rotational symmetry (2)) within a metal box (3).

An alternative embodiment to the dielectric resonator is a resonant cavity of which several are known to those skilled in the art. One simple and efficient resonant cavity is a metal box, such as a cylindrical metal box. A suitable mode is the one known as TM1,1,0 which produces a perpendicular magnetic field on the axis of the cavity. It is possible to excite two such modes in the same cavity at the same frequency producing fields which are mutually perpendicular. By arranging them to have a 90° phase difference a rotating field can be produced which is especially efficient for implementing dynamic polarisation with a minimum of dissipation in the sample. Modes with similar field distributions for different shapes of cavities e.g. rectangular cavities are familiar to those skilled in the art.

In a further embodiment of the method and apparatus according to this aspect of the invention, the composition may be dispersed into a plurality of compartments during the dynamic nuclear polarisation step. Thus the composition might be typically divided into parallel channels provided, for example, by parallel separating plates, discs or tubes, typically open-ended tubes. The electric losses (eddy currents) in the composition caused by the magnetic field are decreased by dividing the composition into smaller volumes using electrically isolating barriers, preferably situated perpendicular to the field. If the composition is in a cylindrical vessel surrounded by a dielectric resonator as described hereinbefore, the isolating barriers would be planes passing radially from the vessel axis to its wall. A simpler and more practical arrangement is to polarise the composition in a container which contains a plurality of thin-walled tubes of an isolating material such as quartz, glass or plastic. This has the advantage of reducing the electric losses in the composition which allows a larger volume of composition to be polarised for the same applied electromagnetic power.

It is envisaged that in the method according to this aspect of the invention, use may be made of any known OMRI contrast agent capable of effecting a diagnostically effective contrast enhancement in the sample to which the MR imaging agent is administered. Where the OMRI contrast agent is a paramagnetic free radical, the radical may be conveniently prepared in situ from a stable radical precursor by a conventional physical or chemical radical generation step shortly before the method according to this aspect of the invention is effected. This is particularly advantageous where the radical has a short half-life. In these cases, the radical will normally be non-reusable and may conveniently be discarded once the separation step of the method according to this aspect of the invention has been completed. Preferred OMRI contrast agents for use in the method according to the invention are those which exhibit low inherent ESR linewidths, preferably less than 500 mG, particularly preferably less than 400 mG, especially preferably less than 150 mG. Generally speaking, organic free radicals such as triarylmethyl, nitroxide ($R_2NO$) radicals (such as porphyrexide, TEMPO, TEMPONE and TEMPOL, see below), nitrogen centred radicals (such as diphenylpicrylhydrazyl (DPPH), see below), oxygen centred radicals (such as Galvinoxyl, see below), stable carbon centred radicals (such as trityls, see below, and allyls), metal ions with unpaired electrons (such as Cr(V) (e.g. BHHA-Cr(V) and EHBA-Cr(V), see below), Mn(II) (e.g. $MnCl_2$), Tm(II), Yb(III), Nd(III), V(IV), Ni(II) and Fe(III) ions), radiation generated radical centres and biradicals provide the most likely source of such desirably low linewidths eg. those described in WO-A-88/10419, WO-A-90/00904, WO-A-91/12024, WO-A-93/02711 or WO-A-96/39367.

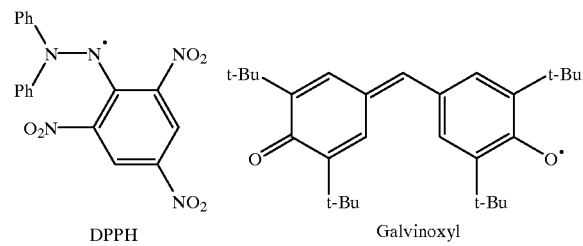

DPPH        Galvinoxyl

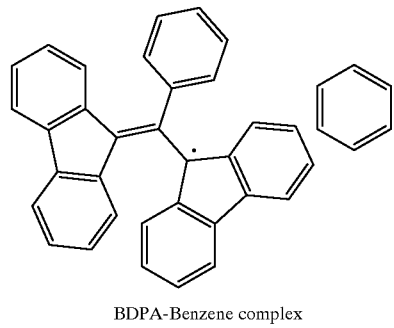

BDPA-Benzene complex

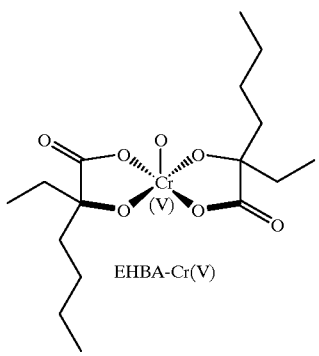

EHBA-Cr(V)

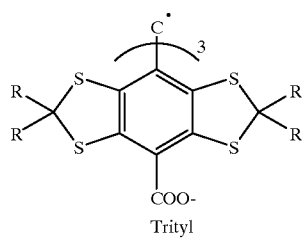

Trityl

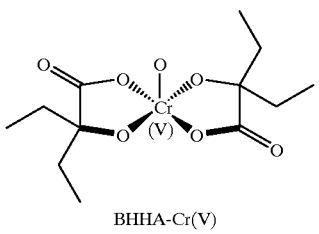

BHHA-Cr(V)

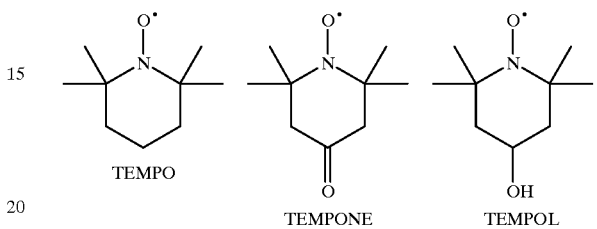

TEMPO     TEMPONE     TEMPOL

However, OMRI contrast agents useful in the present method are not limited to paramagnetic organic free radicals. Particles exhibiting the magnetic properties of superparamagnetism, ferromagnetism or ferrimagnetism may also be useful OMRI contrast agents, as may be other particles having associated free electrons. Superparamagnetic nanoparticles (eg. iron or iron oxide nanoparticles) may be particularly useful. Magnetic particles have the advantages over organic free radicals of high stability and a strong electronic/nuclear spin coupling leading to greater Overhauser enhancement factors.

The method according to this aspect of the invention has the benefit of being able to provide significant spatial weighting to a generated image. In effect, the administration of a polarised MR imaging agent to a selected region of a sample (eg. by injection) means that the contrast effect is, in general, localised to that region. This of course depends on the extent of biodistribution over the period in which the MR imaging agent remains significantly polarised. In general, specific body volumes (i.e. regions of interest) may be defined with improved signal to noise properties of the resulting images in these volumes.

In one embodiment, a "native image" of the sample (e.g. body) (ie. one obtained prior to administration of the MR imaging agent or one obtained for the administered MR imaging agent without prior Overhauser enhancement as in a conventional MR experiment) may be generated to provide structural (eg. anatomical) information upon which the image obtained in the method according to this aspect of the invention may be superimposed. This is a particularly useful aspect of the present method given that the polarisation of the MR imaging agent may only last for a short period and so biodistribution within the timescale of the measurement may be limited.

Given that the method of this aspect of the invention should be carried out within the time that the MR imaging agent remains significantly polarised, once separation has been achieved it is desirable for administration of the MR imaging agent to be effected rapidly and for the MR measurement to follow shortly thereafter. This means that the sample (eg. body or organ) should be available close to the area in which the polarisation has been carried out. The preferred administration route for the MR imaging agent is by injection (eg. bolus injection) or where the lungs are to be imaged by spray, eg. aerosol spray.

The MR imaging agents may be conveniently formulated with conventional pharmaceutical or veterinary carriers or excipients. MR imaging agent formulations manufactured or used according to this invention may contain, besides the MR imaging agent, formulation aids such as are conventional for therapeutic and diagnostic compositions in human or veterinary medicine. Thus the formulation may for example include stabilizers, antioxidants, osmolality adjusting agents, solubilizing agents, emulsifiers, viscosity enhancers, buffers, etc. Preferably none of such formulation aids will be paramagnetic, superparamagnetic, ferromagnetic or ferrimagnetic. The formulation may be in forms suitable for parenteral (eg. intravenous or intraarterial) or enteral (eg. oral or rectal) application, for example for application directly into body cavities having external voidance ducts (such as the lungs, the gastrointestinal tract, the bladder and the uterus), or for injection or infusion into the cardiovascular system. However solutions, suspensions and dispersions in physiological tolerable carriers (eg. water) will generally be preferred.

For use in in vivo imaging, the formulation, which preferably will be substantially isotonic, may conveniently be administered at a concentration sufficient to yield a 1 micromolar to 1000 mM concentration of the MR imaging agent is in the imaging zone; however the precise concentration and dosage will of course depend upon a range of factors such as toxicity, the organ targeting ability of the MR imaging agent, and the administration route. The optimum concentration for the MR imaging agent represents a balance between various factors. In general, optimum concentrations would in most cases lie in the range 10 to 10000 mM, especially 20 to 200 mM, more especially 20 to 1000 mM.

Parenterally administrable forms should of course be sterile and free from physiologically unacceptable agents, and should have low osmolality to minimize irritation or other adverse effects upon administration and thus the formulation should preferably be isotonic or slightly hypertonic. Suitable vehicles include aqueous vehicles customarily used for administering parenteral solutions such as Sodium Chloride solution, Ringer's solution, Dextrose solution, Dextrose and Sodium Chloride solution, Lactated Ringer's solution and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The compositions can contain preservatives, antimicrobial agents, buffers and antioxidants conventionally used for parenteral solutions, excipients and other additives which are compatible with the MR imaging agents and which will not interfere with the manufacture, storage or use of the products.

Where the MR imaging agent is to be injected, it may be convenient to inject simultaneously at a series of administration sites such that a greater proportion of the vascular tree may be visualized before the polarization is lost through relaxation.

The dosages of the MR imaging agent used according to the method of this aspect of the present invention will vary according to the precise nature of the MR imaging agents used, of the tissue or organ of interest and of the measuring apparatus. Preferably the dosage should be kept as low as possible while still achieving a detectable contrast effect. In general, the maximum dosage will depend on toxicity constraints.

For the purposes of administration, the MR imaging agent should be preferably administered in the absence of the whole of, or substantially the whole of, the OMRI contrast agent. Preferably at least 80% of the OMRI contrast agent is removed, particularly preferably 90% or more, especially preferably 95% or more, most especially 99% or more. In general, it is desirable to remove as much OMRI contrast agent as possible prior to administration to improve physiological tolerability and to increase $T_1$. Thus preferred OMRI contrast agents for use in the present invention are those which can be conveniently and rapidly separated from the polarised MR imaging agent using known techniques as discussed below. However where the OMRI contrast agent is non-toxic, the separation step may be omitted. A solid (eg. frozen) composition comprising an OMRI contrast agent and an MR imaging agent which has been subjected to polarisation may be rapidly dissolved in saline (eg. warm saline) and the mixture injected shortly thereafter.

In the separation step of the method of the invention, it is desirable to remove substantially the whole of the OMRI contrast agent from the composition (or at least to reduce it to physiologically tolerable levels) as rapidly as possible. Many physical and chemical separation or extraction techniques are known in the art and may be employed to effect rapid and efficient separation of the OMRI contrast agent and MR imaging agent. Clearly the more preferred separation techniques are those which can be effected rapidly and particularly those which allow separation in less than one second. In this respect, magnetic particles (eg. superparamagnetic particles) may be advantageously used as the OMRI contrast agent as it will be possible to make use of the inherent magnetic properties of the particles to achieve rapid separation by known techniques. Similarly, where the OMRI contrast agent or the particle is bound to a solid bead, it may be conveniently separated from the liquid (i.e. if the solid bead is magnetic by an appropriately applied magnetic field).

For ease of separation of the OMRI contrast agent and the MR imaging agent, it is particularly preferred that the combination of the two be a heterogeneous system, eg. a two phase liquid, a solid in liquid suspension or a relatively high surface area solid substrate within a liquid, eg. a solid in the form of beads fibres or sheets disposed within a liquid phase MR imaging agent. In all cases, the diffusion distance between the MR imaging agent and OMRI contrast agent must be small enough to achieve an effective Overhauser enhancement. Certain OMRI contrast agents are inherently particulate in nature, eg. the paramagnetic particles and superparamagnetic agents referred to above. Others may be immobilized on, absorbed in or coupled to a solid substrate or support (eg. an organic polymer or inorganic matrix such as a zeolite or a silicon material) by conventional means. Strong covalent binding between OMRI contrast agent and solid substrate or support will, in general, limit the effectiveness of the agent in achieving the desired Overhauser effect and so it is preferred that the binding, if any, between the OMRI contrast agent and the solid support or substrate is weak so that the OMRI contrast agent is still capable of free rotation. The OMRI contrast agent may be bound to a water insoluble substrate/support prior to the polarisation or the OMRI contrast agent may be attached/bound to the substrate/support after polarisation. The OMRI contrast agent may then be separated from the MR imaging agent e.g. by filtration before administration. The OMRI contrast agent may also be bound to a water soluble macromolecule and the OMRI contrast agent-macromolecule may be separated from the MR imaging agent before administration.

Where the combination of an OMRI contrast agent and MR imaging agent is a heterogeneous system, it will be possible to use the different physical properties of the phases to carry out separation by conventional techniques. For example, where one phase is aqueous and the other non-aqueous (solid or liquid) it may be possible to simply decant one phase from the other. Alternatively, where the OMRI contrast agent is a solid or solid substrate (eg. a bead)

suspended in a liquid MR imaging agent the solid may be separated from the liquid by conventional means eg. filtration, gravimetric, chromatographic or centrifugal means. It is also envisaged that the OMRI contrast agents may comprise lipophilic moieties and so be separated from the MR imaging agent by passage over or through a fixed lipophilic medium or the OMRI contrast agent may be chemically bound to a lipophilic solid bead. The MR imaging agent may also be in a solid (eg. frozen) state during polarisation and in close contact with a solid OMRI contrast agent. After polarisation it may be dissolved in heated water or saline or melted and removed or separated from the OMRI contrast agent where the latter may be toxic and cannot be administered.

One separation technique makes use of a cation exchange polymer and a cationic OMRI contrast agent, eg. a triarylmethyl radical carrying pendant carboxylate groups. Alternatively acidifying the solution to around pH 4 may cause the OMRI contrast agent to precipitate out. Separation may then be carried out for example by filtration followed by neutralisation. An alternative technique involves adding ions which causes precipitation of ionic OMRI agents which may then be filtered off.

Certain OMRI contrast agents, such as the triarylmethyl radical, may have an affinity for proteins. Thus, after polarisation, a composition containing an OMRI contrast agent with a protein affinity may be passed through or over a protein in a form which exposes a large surface area to the agent eg. in particulate or surface bound form. In this way, binding of the OMRI contrast agent to the protein enables it to be removed from the composition.

Alternatively when a hydrophilic MR imaging agent is in a solid (eg. frozen) form it may be brought into contact with a hydrophobic OMRI contrast agent which is dissolved in an organic fluid with a melting temperature higher than the MR imaging agent. The mixture is frozen and polarisation performed. After polarisation, the mixture is heated and the solid OMRI contrast agent and its solvent are removed. The MR imaging agent will remain hyperpolarised for a significant time in the frozen state and may be transported long distances before being dissolved in water or saline for injection.

What is claimed is:

1. A method of MR investigation of a sample said method comprising:
    (i) placing in a uniform magnetic field a composition comprising an Overhauser magnetic resonance imaging (OMRI) contrast agent and a magnetic resonance (MR) imaging agent containing in its molecular structure nuclei capable of emitting magnetic resonance signals and having a $T_1$ relaxation time of 6 s or more, when at 37° C. in $D_2O$ in a field of 7T;
    (ii) exposing said composition to a first radiation of a frequency selected to excite electron spin transitions in said OMRI contrast agent and thereby cause a nuclear spin polarisation of said nuclei;
    (iii) optionally but preferably separating the whole, substantially the whole, or a portion of said OMRI contrast agent from said MR imaging agent;
    (iv) administering said MR imaging agent to said sample;
    (v) exposing said sample to a second radiation of a frequency selected to excite nuclear spin transitions;
    (vi) detecting magnetic resonance signals from said sample; and
    (vii) optionally, generating an image or dynamic flow data from said detected signals.

2. A method of MR investigation of a sample said method comprising:
    (i) placing in a uniform magnetic field a composition comprising an Overhauser magnetic resonance imaging (OMRI) contrast agent and a magnetic resonance (MR) imaging agent containing in its molecular structure nuclei, capable of emitting magnetic resonance signals, and having a $T_1$ relaxation time of 6 s or more, when at 37° C. in $D_2O$ in a field of 7T;
    (ii) exposing said composition to a first radiation of a frequency selected to excite electron spin transitions in said OMRI contrast agent and thereby cause a nuclear spin polarisation of said nuclei;
    (iii) separating the whole, substantially the whole, or a portion of said OMRI contrast agent from said MR imaging agent;
    (iv) administering said MR imaging agent to said sample;
    (v) exposing said sample to a second radiation of a frequency selected to excite nuclear spin transitions; and
    (vi) detecting magnetic resonance signals from said sample.

3. A method as claimed in claim 2 wherein said MR imaging agent has $T_1 > 8$ s.

4. A method as claimed in claim 2 wherein said MR imaging agent has $T_1 > 10$ s.

5. A method as claimed in claim 2 wherein said MR imaging agent has $T_1 > 15$ s.

6. A method as claimed in claim 2 wherein said MR imaging agent has $T_1 > 30$ s.

7. A method as claimed in claim 2 wherein said MR imaging agent has $T_1 > 70$ s.

8. A method as claimed in claim 2 wherein said MR imaging agent has $T_1 > 100$ s.

9. A method as claimed in claim 2 wherein said MR imaging agent has a long $T_2$ relaxation time.

10. A method as claimed in claim 2 wherein said MR imaging agent is stored in frozen form once polarised and prior to step (iv) of claim 1 is heated to physiological temperatures.

11. A method as claimed in claim 2 further comprising a final step (vii) of generating an image or dynamic flow data from said detected signals produced via step (vi).

12. An imaging composition comprising an Overhauser magnetic resonance imaging (OMRI) contrast agent and a magnetic resonance (MR) imaging agent having a $T_1$ relaxation time of greater than 100 s, when at 37° C. in $D_2O$ in a field of 7T.

* * * * *